(12) United States Patent
Levy et al.

(10) Patent No.: US 11,707,217 B2
(45) Date of Patent: Jul. 25, 2023

(54) DIAGNOSIS AND EFFECTIVENESS OF MONITORING ATTENTION DEFICIT HYPERACTIVITY DISORDER

(71) Applicant: Iluria Ltd., Hod Hasharon (IL)

(72) Inventors: Hagay Levy, Hod Hasharon (IL); Birkat Klimshtein Levy, Hod Hasharon (IL)

(73) Assignee: Iluria Ltd., Hod Hasharon (IL)

( * ) Notice: Subject to any disclaimer, the term of this patent is extended or adjusted under 35 U.S.C. 154(b) by 239 days.

(21) Appl. No.: 16/959,212

(22) PCT Filed: Jan. 7, 2020

(86) PCT No.: PCT/IB2020/050088
§ 371 (c)(1),
(2) Date: Jun. 30, 2020

(87) PCT Pub. No.: WO2020/144575
PCT Pub. Date: Jul. 16, 2020

(65) Prior Publication Data
US 2021/0196175 A1 Jul. 1, 2021

Related U.S. Application Data

(60) Provisional application No. 62/789,605, filed on Jan. 8, 2019.

(51) Int. Cl.
*G16H 50/70* (2018.01)
*G16H 50/20* (2018.01)
(Continued)

(52) U.S. Cl.
CPC .......... *A61B 5/168* (2013.01); *A61B 5/02055* (2013.01); *A61B 5/4848* (2013.01);
(Continued)

(58) Field of Classification Search
CPC ................................................ G06Q 50/20–26
See application file for complete search history.

(56) References Cited

U.S. PATENT DOCUMENTS

| 2003/0100844 A1* | 5/2003 | Miller | A61B 5/168 |
| | | | 600/545 |
| 2003/0171658 A1* | 9/2003 | Keirsbilck | A61B 5/01 |
| | | | 600/300 |

(Continued)

FOREIGN PATENT DOCUMENTS

| WO | 2016/110804 | 7/2016 |
| WO | 2018/039610 | 3/2018 |

OTHER PUBLICATIONS

Xioa, Cao "Optimization and Machine Learning Methods for Medical and Healthcare Applications" University of Washington, ProQuest 10244899 (Year: 2017).*

(Continued)

*Primary Examiner* — Neal Sereboff
(74) *Attorney, Agent, or Firm* — Dekel Patent Ltd.; David Klein

(57) ABSTRACT

A method and a system are provided for taking biomarker measurements of patients who have ADHD. Mathematical analysis (e.g., pattern recognition, machine learning and AI algorithms) of the biomarker measurements is used to create a unique personal prediction model and data set for an individual patient. The unique personal data set is used to diagnose and monitor a particular problem of the individual patient associated with ADHD, or to recommend a treatment for a particular problem of the individual patient associated with ADHD, or to predict an outcome of a treatment for a particular problem of the individual patient associated with ADHD.

9 Claims, 7 Drawing Sheets

(51) Int. Cl.
   *G16H 20/70*   (2018.01)
   *A61B 5/16*    (2006.01)
   *G06N 20/00*   (2019.01)
   *A61B 5/0205*  (2006.01)
   *A61B 5/00*    (2006.01)

(52) U.S. Cl.
   CPC ............ *A61B 5/7267* (2013.01); *G06N 20/00* (2019.01); *G16H 20/70* (2018.01); *G16H 50/20* (2018.01); *G16H 50/70* (2018.01); *A61B 2560/0228* (2013.01)

(56) References Cited

U.S. PATENT DOCUMENTS

| 2017/0000400 | A1* | 1/2017 | Gordon | A61B 5/165 |
| 2019/0214145 | A1* | 7/2019 | Kurek  | A61K 31/366 |
| 2020/0297265 | A1* | 9/2020 | Fourie | G16H 50/70 |
| 2021/0169417 | A1* | 6/2021 | Burton | A61B 5/4857 |

OTHER PUBLICATIONS

PCT Search Report and Written Opinion PCT/IB2020/050088, dated May 12, 2020.

Yasumura et al., "Applied Machine Learning Method to Predict Children With ADHD Using Prefrontal Cortex Activity: A Multicenter Study in Japan", J Atten Disord. Nov. 1, 2017;1087054717740632. doi: 10.1177/1087054717740632.

Powers et al., "Evaluating Disease Prediction Models Using a Cohort Whose Covariate Distribution Differs From That of the Target Population", Stat Methods Med Res. Jan. 2019;28(1):309-320. doi: 10.1177/0962280217723945. Epub Aug. 16, 2017.

Bae et al., "Pilot Study: An Ocular Biomarker for Diagnosis of Attention Deficit Hyperactivity Disorder", Psychiatry Investig. May 2019;16(5):370-378. doi: 10.30773/pi.2019.02.26.1. Epub May 23, 2019.

* cited by examiner

Pearson correlation – correlation between a subset of possible features. Most features are weakly to moderately correlated, suggesting they contribute non-overlapping information RELATIVE IMPACT ON DISCRIMINANT VECTOR #1
FDA Loadings – the contribution of each feature to the first discriminant vector
Significant contributions are observed for IBI, HR, Acceleration and EDA

DIAGNOSIS AND EFFECTIVENESS OF MONITORING ATTENTION DEFICIT HYPERACTIVITY DISORDER

FIELD OF THE INVENTION

The present invention generally relates to a method of analyzing a subject for Attention Deficit Hyperactivity Disorder (ADHD), and particularly, but not limited to, determining ADHD diagnosis and the effectiveness of the medication, appropriate dosage taken to counteract ADHD or other related clinical treatments.

BACKGROUND OF THE INVENTION

Attention Deficit Hyperactivity Disorder (ADHD) is a disorder that inhibits an individual's capacity to regulate activity level, inhibit behavior, and attend to tasks. ADHD is the most common developmental disorder of childhood, affecting 5-15% of school age children, or approximately 6.4 million children in the United States. ADHD affects not just school-aged children but also adults who are medically treated. ADHD may interfere with the ability to learn or to develop satisfactory interpersonal relationships and may result in academic failure, inability to fulfill intellectual potential, poor self-esteem, or socially maladaptive behavior. In general, when ADHD is left untreated there is a gradual accumulation of adverse processes and events that increase the risk of serious psychopathology later in life.

The current ADHD diagnosis in patients is subjective and varies according to the method and opinions of the specialist. Generally, it involves interviewing the patients, parents, teachers, and school staff, etc. The specialist will then incorporate and analyze all of the data obtained and make a decision based on his/her findings. In some cases, the diagnosis process involves computerized tasks which provides scores for attention, hyperactivity and impulsivity.

ADHD is a difficult disorder to diagnose. ADHD children may experience significant functional problems, such as school difficulties, academic underachievement, poor relationships with family and peers, and low self-esteem. Adults with ADHD often have a history of losing jobs, impulsive actions, substance abuse, and broken marriages. ADHD often goes undiagnosed if not caught at an early age and affects many adults who may not be aware of the condition. ADHD has many look-alike causes (family situations, motivations) and co-morbid conditions (depression, ODD (oppositional defiant disorder), anxiety, and learning disabilities) are common.

ADHD treatment has two main phases:
a. Initial diagnosis and setting up initial recommended treatment (e.g., type of medication and dosage)
b. Ongoing treatment monitoring, as the patient's physiology constantly changes and the treatment should be adjusted.

The current ADHD diagnosis is done at a clinic using various methods. Generally, it involves interviewing the patients, parents, teachers, and school staff, etc. The specialist will then incorporate and analyze all of the data obtained and make a decision based on his/her findings. In some cases, the diagnosis process involves ratings or scores for attention, hyperactivity and impulsivity.

ADHD is a difficult disorder to diagnose. Moreover, once a patient is diagnosed, the continuous monitoring process is completely trial-and-error based, relying on subjective and questionnaire-based reporting provided by different stakeholders (e.g. school teacher).

In addition to the above, both diagnosis and monitoring phases do not relate to different patient clusters. Currently, other than age and weight classes, ADHD patients are not grouped into clusters with similar physiological attributes within each cluster. As a result, the initial drug allocation and ongoing adjustments are based solely on the patient's age and weight, with no other objective additional physiological elements.

There is thus a need for a passive, objective, inexpensive, and reliable technique for determining ADHD continuous diagnosis and the effectiveness of the medication, appropriate dosage taken to monitor and counteract ADHD and other clinical treatments.

SUMMARY OF THE INVENTION

The present invention seeks to provide a method, and a tracking and evaluation algorithmic system, for determining continuous ADHD diagnosis, monitoring and evaluation of the effectiveness of the medication and appropriate dosage taken to counteract ADHD or other clinical treatments. The method and system include ADHD patients' clustering and continuous, personalized monitoring of ADHD treatment effectiveness using mathematical analysis of a series of biomarker measurements.

As opposed to the prior art, the biomarker measurements are used to define clusters of patients and create a personal profile, baseline and prediction pattern per patient. The patients in each cluster have similar attributes (e.g., sex (for example, all patients in the cluster are female), age range (for example, all patients in the cluster are in an age range of 10-15 years old), comorbidities (for example, all patients in the cluster suffer from two same disorders, such as anxiety and depression) and biomarker measurements that are similar, so that a variance in said biomarker measurements used to create said cluster is significantly smaller than a variance in biomarker measurements of patients not in said cluster. The unique personal model is calibrated by machine and deep learning techniques which are specifically assigned to patient cluster and specifically calibrated per patient, for the provision of output that assess the clinical and behavioral indicators of ADHD.

BRIEF DESCRIPTION OF THE DRAWINGS

The present invention will be understood and appreciated more fully from the following detailed description, taken in conjunction with the drawings in which:

FIGS. 1 and 2 are simplified illustrations of personal calibration weighting used in a non-limiting embodiment of the methods and system of the present invention, wherein FIG. 1 shows the Pearson correlation between a subset of possible features, showing that the markers are not correlated, hence are valuable predictors, and FIG. 2 shows the contribution of each feature to the first discriminant vector, illustrating the personal model calibration per specific patient. In FIG. 2, IBI is inter-bit interval (between heart rate peaks), EDA is galvanic skin response and acceleration is that of the patient or a portion of the patient.

DETAILED DESCRIPTION OF EMBODIMENTS

Figure 1:
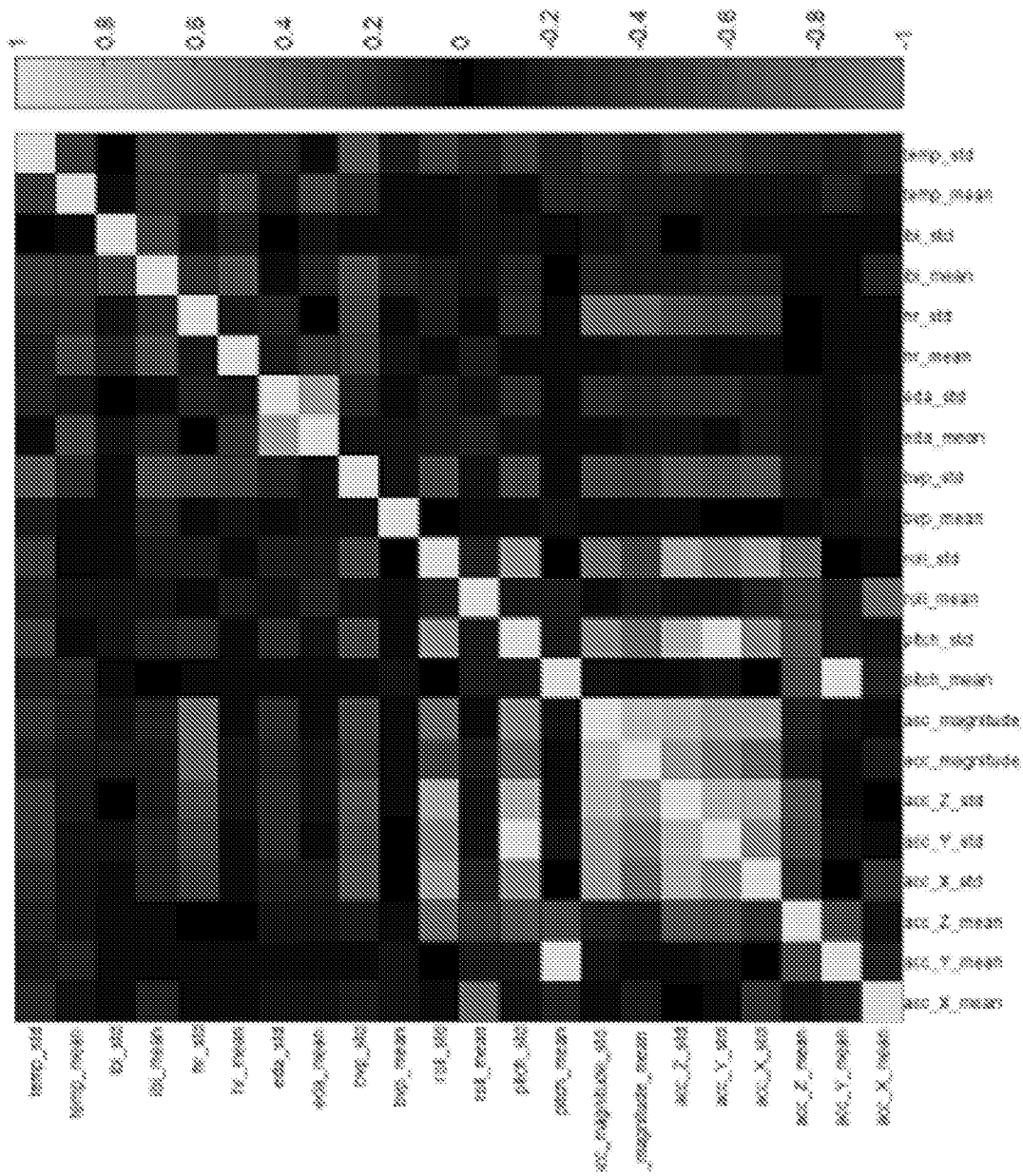

As mentioned above, in contrast to the prior art, the present invention uses mathematical analysis of biomarker measurements to define clusters of patients and, for each patient, to create a personal profile, baseline and prediction pattern. The unique personal model is calibrated by machine and deep learning techniques which are specifically assigned per patient, for the provision of output that assess the clinical and behavioral indicators of ADHD.

The personal method may include the followings steps:
A: Cluster Allocation:
Using patients' measured biomarker data to build an ensemble of predictive models for Diagnostic and Statistics manual-V (DSM-V) compliant clinical ADHD diagnosis scores used by physicians. This step uses biomarker data measured during the DSM-V compliant clinical diagnosis process, and would use a host of pattern recognition, machine learning and AI algorithms.
Using pattern recognition, machine learning and AI algorithms to cluster patients based on external features (such as sex, age, comorbidities) and internal features (biomarker data), and to modify the predictive model to each cluster.
B: Personal Baseline Calibration and Continues Monitoring:
Using pattern recognition, machine learning and AI algorithms to calibrate model features (e.g., biomarkers weighting and/or selecting the importance of a particular physiological feature) and tailor a predictive model to each individual, based on its cluster association and on its unique combination of external and internal features.
Using the trained personalized predictive model to automatically and passively monitor patients for their response to ADHD treatment.
C: Ongoing Calibration:
The predictive models are automatically updated and improved (continuous learning) with more biomarker data measured for each patient.

The above setups of the indicators are based on the criteria established by the American Medical Association (AMA) as described in the Diagnostic and Statistics manual-V (DSM-V).

The method also assesses the objective impact of other treatment options for ADHD patients, such as neurofeedback and various behavioral treatments.

The output of the method is achieved by demonstrating personal machine learning based prediction model and personal baseline of the individual with and without effective treatment, pertaining to the DSM-V criteria, including relation to each of the ADHD disorder aspects: attention, hyperactivity and impulsivity. This output supports physicians' evaluation of treatment success and provides additional, ongoing analysis which recommends possible advantageous treatment modifications.

The method uses pattern recognition, machine learning, AI algorithms, and other techniques. It is based on biomarker measurements (described below) and external information (such as sex, age, etc.). A predictive model is designed upon collection of all samples, then modified within each cluster of patients, and then further modified to match the specific personal pattern of every patient. Eventually, every individual patient is characterized by a unique, personalized, predictive model.

The following is a description of one non-limiting embodiment of the method and system of the invention.

First, a combination of the following of biomarkers' measurements may be automatically collected and recorded by a device, such as a wearable device:

| | |
|---|---|
| PPG | nano watt |
| Inter beat interval | Sec |
| Heart rate (BPM) | Sec |
| Skin temperature | Celsius ° C. |
| Accelerometer (or motion sensor) | gravity (g) |
| Heart Rate Variability | hertz (Hz) |
| Gyro | degrees per second (°/s) |
| Respiratory rate | BRA |
| Blood pressure | mmHg |
| EEG | μV |
| Skin conductance | Hz |
| ECG | mV/mS |
| Blood oxygen saturation | $SaO_2$ |
| Systemic vascular resistance | PRU |

Afterwards, patients may be assigned to a pre-defined cluster using the biomarkers and physiological attributes. For example, initial ongoing biomarkers measurement, together with patient's attributes (e.g., girl, 15 years old, Afro-American, with birth difficulties) may be used to assign a patient into a designated cluster. The method may start with a certain number of clusters, and in parallel there may be ongoing cluster calibration and addition of new clusters.

The methods for clustering and for building predictive models may be based on an ensemble of models, including linear models (e.g., Fisher Discriminant Analysis and Linear Discriminant analysis) and nonlinear ones (e.g., neural network classifiers, random forests). The ensemble of models may be adjusted and constantly re-trained whenever more patient data become available.

The method may also include measuring biomarkers in parallel to physician diagnostics. For example, the measurement may be carried out together with DSM-V based clinical evaluation to associate biomarkers with attention, hyperactivity and impulsivity.

The method may also include calculation of a personal calibration model. The method may assign a personal calculation model to setup baseline and ongoing prediction models. (Two examples are given below.)

The method may also include setting up personalized biomarkers weightings and significance level. For example, these may include personal biomarker weighting and/or selecting the importance of a particular feature while assessing non-linear models.

The method may also include both monitoring ongoing treatment and/or preliminary ADHD diagnosis. This may include utilizing personal prediction patterns and performing ongoing analysis using machine learning based process.

The method may also include ongoing cluster calibration and shifts between clusters. For example, there may be ongoing evaluation of the patient to decide whether he/she should shift between clusters (e.g., age group changed from 7-10 to 11-14), or there may be ongoing creation of new clusters or sub-clusters.

Personal Process—Samples Demonstrating the Significance of Personal Modeling:

The importance of personal modeling is now explained with reference to FIGS. 1-7. The figures relate to measurements of two ADHD patients, both from the same cluster (in which Fisher Discriminant Analysis was used as a search method). A personal baseline was created for both patients. The presented baseline calculations illustrate three stages of examination—without medication, with ineffective medication and with effective medication.

Figure 2:
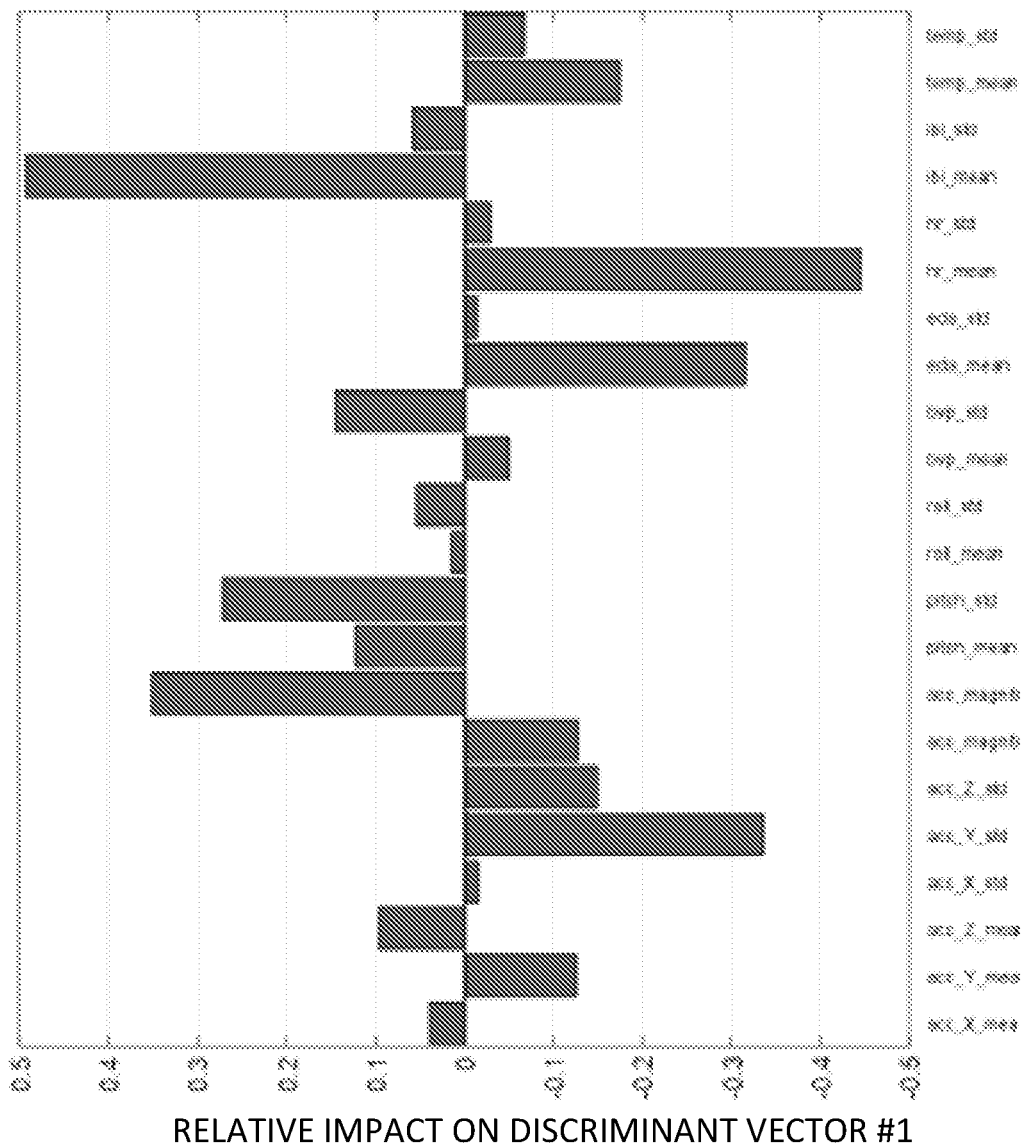

Patient 1:

Personal calibration weighting was assigned as seen in FIGS. 1 and 2. FIG. 1 shows the Pearson correlation between a subset of possible features. FIG. 2 shows the contribution of each feature to the first discriminant vector.

Figure 3:
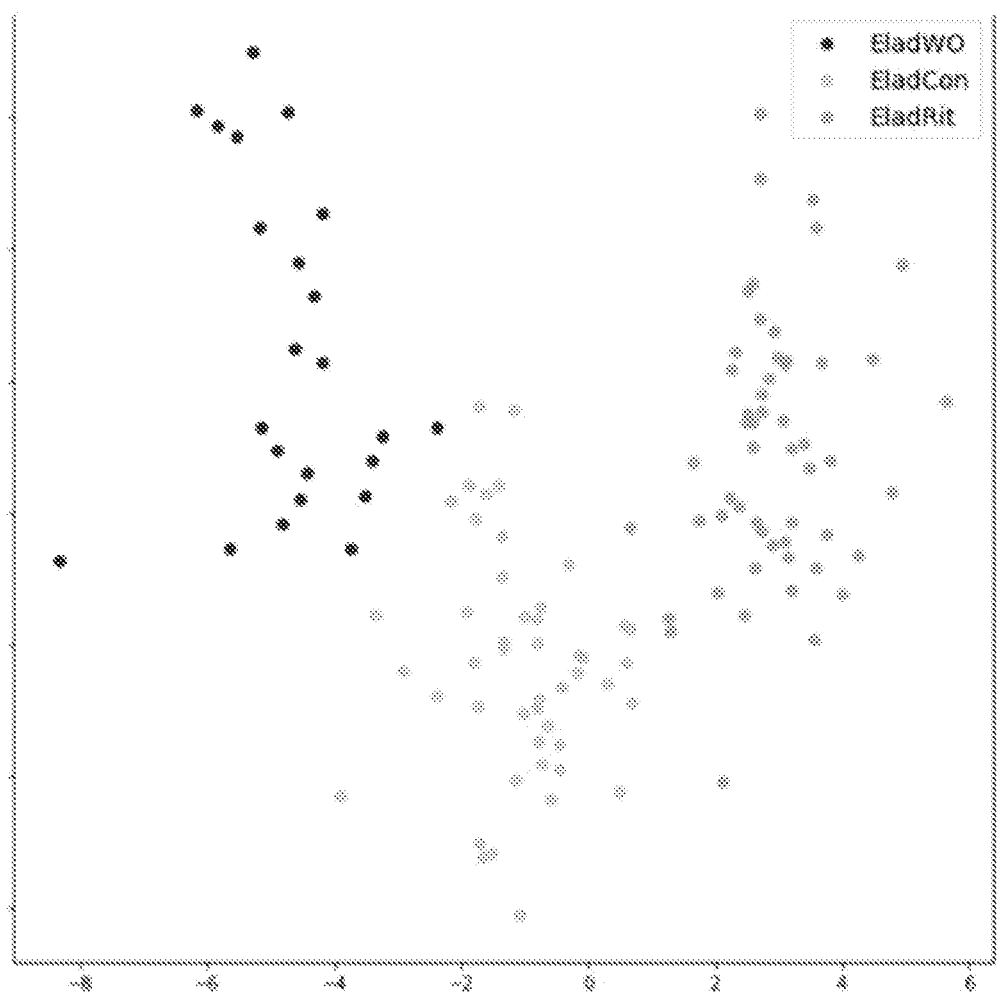
FIG. 3 is a simplified illustration of using a personal calibration model to setup a personal baseline for monitoring medical treatment effectiveness.

Using the personal calibration model, the personal baseline was set up in accordance with the physician DSM-V diagnosis (X represents medication effectiveness). This is shown in FIG. 3.

Figure 4:
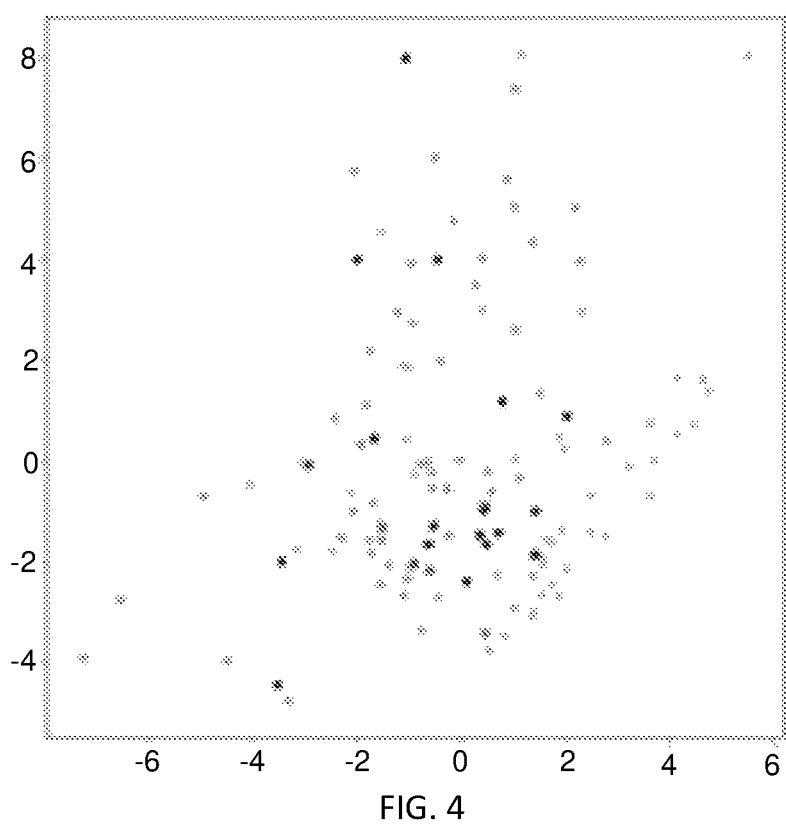
FIG. 4 is a simplified illustration of implementation of the Patient 1 personal model on Patient 2, both from the same cluster, and shows that this proved to be incapable of separating the significance of the biomarkers and incapable of setting up a personal baseline without personal calibration.

Patient 2:

After training the model and applying it on Patient 2 (Patients 1 and 2 are both from the same cluster), direct implementation of the Patient 1 personal calibration (weighting of biomarkers) on Patient 2 proved incapable of creating DSM-V compliant data clusters and incapable of setting up a personal baseline (as both patients are from the same cluster one can notice a slight, but not valid, separation). This is shown in FIG. 4.

Figure 5:
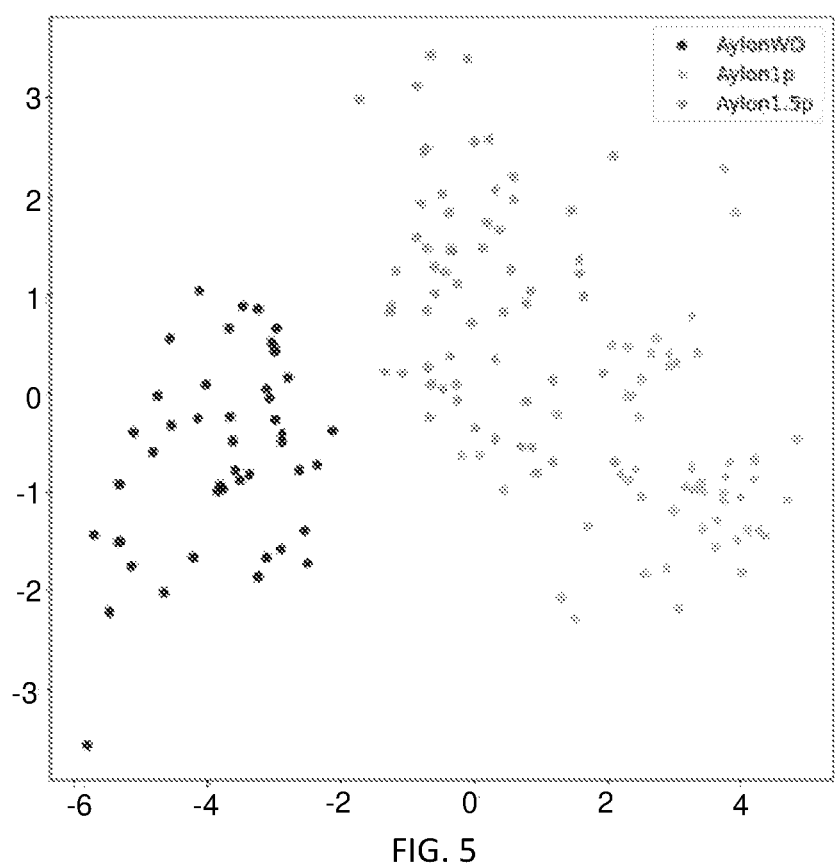
FIG. 5 is a simplified illustration of assigning a personal calibration to the search pattern for Patient 2, which proved successful in setting up a personal baseline in accordance with the physician diagnosis.
Figure 6:
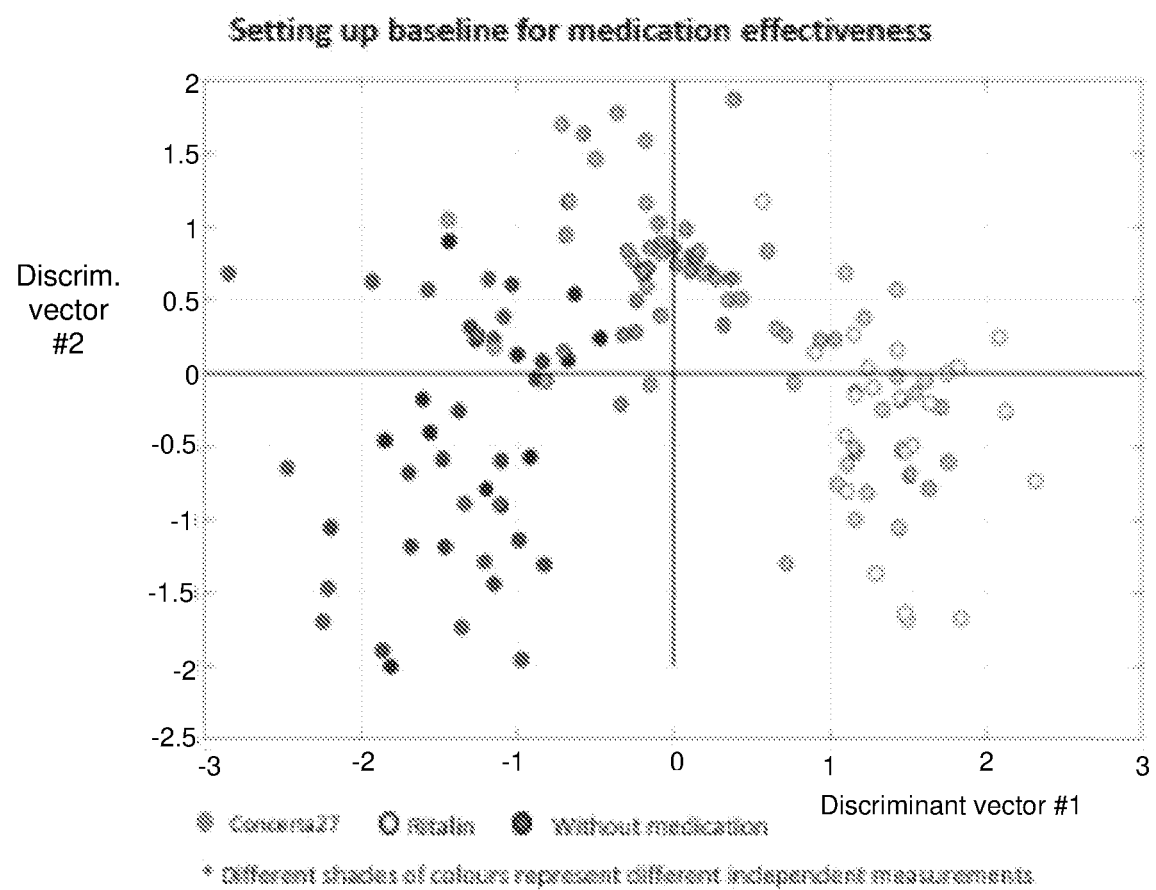
FIGS. 6 and 7 are simplified illustrations of two different examples of personal, ongoing analysis using biomarkers, in accordance with non-limiting embodiments of the invention.
Figure 7:
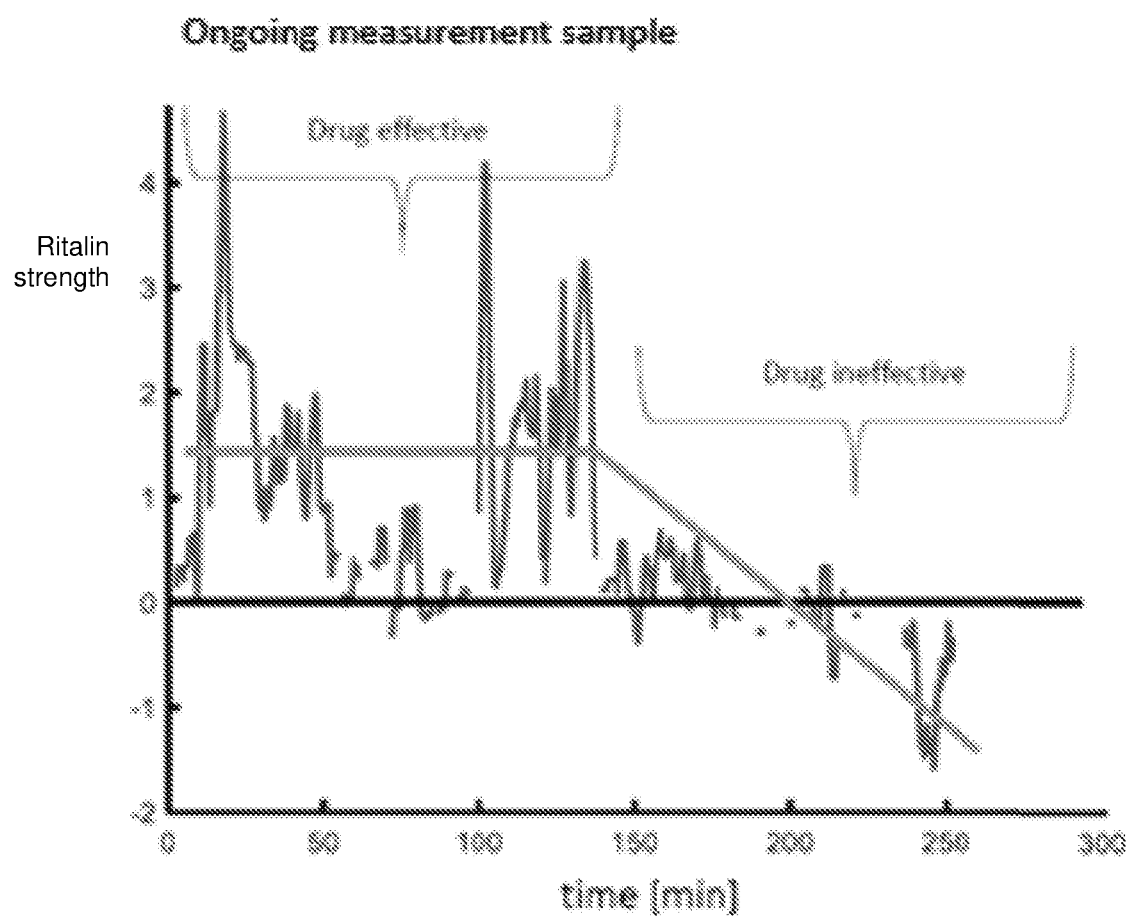

After re-calibrating and assigning a unique personal model for Patient 2, the invention was able, as in Patient 1, to set up the personal baseline in accordance with the physician DSM-V diagnosis (X represents medication effectiveness). This is shown in FIG. 5.

In another clinical trial, a first set of patients were positively diagnosed with ADHD, and some were given an effective medical treatment and some were given no treatment. A second set of patients were positively diagnosed with ADHD and some were given an ineffective medical treatment and some were given no treatment. Both the first set and the second set of patients were analyzed by the system and method of the invention. The system and method correctly identified 100% of the time which patients in the first set were given an effective treatment and close to 100% of the time which ones were given no treatment. The system and method correctly identified close to 100% of the time which patients in the second set were given an ineffective treatment and close to 100% of the time which ones were given no treatment.

Technical Process:

All of the biomarker measurements are automatically collected and recorded by a wearable device. Data may be transformed to a centralized hub. Data may be stored within the wearable device memory for later downloading. Thereafter, the data may be transmitted or uploaded to a digital data repository (cloud or other) and analyzed by implementing machine and deep learning techniques.

System output is a translation of the processed analysis into medical indicators and status reports and is provided to physicians through a medical web application, and to the individuals (patient, child, parents etc.) through a mobile application.

Analysis is seamlessly transferred to the individual's smartphone (or to other communication device), or via a transmitting, add-on dedicated unit for real-time data transmission.

The web application provides the physicians the results of the analysis which include continuous diagnosis and monitoring of ADHD, which may include indication of medication and dosing effectiveness, actual duration of effect, long term patterns and trends and other clinical aspects (e.g., effectiveness of other clinical treatments, effect on the quality of sleep), predictions related to recommended treatment changes, level of patient medication usage, adherence and overall treatment effectiveness snapshots. Thus, the method provides medical professionals big data insights into real-life patient clinical and behavioral patterns.

In addition, the method may use patient clustering analysis to provide deep learning-based recommendations (e.g., preliminary type of recommended medication to be allocated to each cluster for the initial treatment process).

The application provides a clear view of the medication term or effectiveness during the day, and helps prepare and better manage daily activity of the individual, using predictions of ADHD symptoms' levels.

System's Elements/Components:

The system implementing the method is an IoT platform which may include a user-friendly wearable device. The wearable device may include, without limitation, a sensor hub that include sensors for all biomarkers mentioned in the above table, a user interface (e.g., including graphics, sound and vibration methods of interface), and a software application. For example, without limitation, the application may operate the related services and processes to read the sensors, perform the analysis and send the real time feedback through the user interface to the user. This software application may also communicate with the cloud-based software on a real time or a periodic basis, to update the data measured from the sensors in the device.

The system may further include a cloud-based SW tool or other data repository, which aggregates and analyzes the sensors data, updates related algorithms and generates output in dash boards and reports to stakeholders.

The system may further include a web application interface for medical professionals—providing output on diagnosis of ADHD, indication of medication and dosing effectiveness, predictions of recommended treatment changes, level of patient medication usage, adherence and overall treatment effectiveness snapshots.

The system may further include a mobile application interface for users (individuals who have ADHD and stakeholders (e.g. parents) providing a real time view on the individual's ADHD condition throughout the day, including medication cycle impact and phasing out timing, and predictions of ADHD personal patterns.

Method Outputs and Example of the Importance of Personal Analysis:

Tests of the methods of the invention have demonstrated their efficacy, resulting in outputs significantly correlated to the demonstrated clinical results, as indicated by physicians.

The following section provides examples of personal, ongoing analysis using biomarkers.

Examples: Output Samples

Example 1 (shown in FIG. 6): A case of a child treated with CONCERTA27, later switched to RITALIN LA20—classification outputs clearly demonstrate the different success levels of the two medications, aligned with physician's clinical observations (RITALIN: effective, CONCERTA: not). The personal baseline scale for this patient is: (1.5)—no medication, 1.5—effective medical treatment (and, thus, ~0—ineffective medical treatment). The classification is based on multiple biomarkers measurements combined and a personalized formula determining the significance of each marker for this specific patient.

Example 2 (shown in FIG. 7): A description of the result of the processed biomarkers measurement pertaining to the duration of medication effectiveness demonstrating the point in time from which medication impact is drastically reduced. This was found highly correlated with clinical condition of the medication phasing out time, indicating a drastic increase of ADHD symptoms (the baseline for the initial 150 minutes is, as before, 1.5, later on deteriorating to (1.5)).

The method demonstrated significant correlation between the processed biomarkers measurements and the clinical results identified by physicians, in the subjects evaluated.

What is claimed is:

1. A method for implementing an intelligent monitoring of Attention Deficit Hyperactivity Disorder (ADHD) of a subject in a computing environment by a processor, comprising:
receiving biomarker measurements of a plurality of subjects, each of whom has ADHD and has not been given any medication, the biomarker measurements being collected by biomarker sensors comprising a heart rate variability sensor for measuring heart rate variability or inter-bit interval between heart rate peaks, and an accelerometer or gyroscope;
repeating the step of receiving biomarker measurements after each of the subjects has been given a medication for treating ADHD;
executing machine learning logic to create clusters of the subjects, each of said clusters being based on sex, age, and comorbidities of the subjects, and also based on said biomarker measurements made before and after each of the subjects has been given a medication for treating ADHD, wherein for a particular cluster a variance in said biomarker measurements used to create said particular cluster is smaller than a variance in biomarker measurements of patients not in said particular cluster;
executing machine learning logic to learn an effect of the medication for treating ADHD on said biomarker measurements of an individual in said particular cluster, by using discriminant analysis to generate a discriminant vector of a subset of said biomarker measurements that changed more than others of said biomarker measurements for said individual, and using said discriminant vector to create a personal profile for said individual that includes a baseline set of data based on the biomarker measurements before being given said medication and a prediction pattern based on the biomarker measurements after being given said medication;
identifying and recommending one or more treatment changes to be implemented by said individual to increase treatment effectiveness;
receiving subject feedback, as feedback data, with respect to an effectiveness of the one or more treatment changes implemented by said individual; and
executing the machine learning logic to re-learn the effect of the medication for treating ADHD on said biomarker measurements and use the feedback data to iteratively optimize said discriminant vector to enhance effectiveness of future treatment changes recommended to be implemented by said individual.

2. The method according to claim 1, wherein the step of executing machine learning logic to create clusters of the subjects uses said biomarker measurements, which were made before and after each of the subjects has been given said medication for treating ADHD, creates clusters in relation to ADHD disorder aspects including attention, hyperactivity and impulsivity.

3. The method according to claim 1, wherein the step of executing machine learning logic to learn the effect of the medication for treating ADHD on said biomarker measurements of said individual in said particular cluster, learns the effect of the medication for treating ADHD in relation to ADHD disorder aspects including attention, hyperactivity and impulsivity.

4. The method according to claim 1, wherein the method is implemented as an internet of things (IoT) platform that comprises a wearable device, said wearable device comprising a sensor hub that comprises said biomarker sensors, a user interface, and a software application.

5. The method according to claim 4, wherein said software application is used to operate services and processes to read said biomarker sensors, perform analysis and send real time feedback through said user interface to a user.

6. The method according to claim 4, wherein said software application is used to communicate with a cloud-based software on a real time or a periodic basis, to update data measured from said biomarker sensors.

7. The method according to claim 1, wherein said biomarker sensors further comprise at least one of a heart rate sensor, a galvanic skin response sensor, a skin temperature sensor, a photoplethysmogram (PPG) sensor, an electroencephalogram sensor (EEG), an electrocardiogram sensor (ECG), a respiratory rate sensor, a blood pressure sensor, a skin conductance sensor, a blood oxygen saturation sensor, and a systemic vascular resistance sensor.

8. The method according to claim 1, further comprising executing the machine learning logic to perform ongoing cluster calibration and shifts between clusters.

9. A system for implementing the method of claim 1, comprising biomarker sensors for making the biomarker measurements and a processor for performing the steps defined in claim 1.

* * * * *